United States Patent [19]

McNeish et al.

[11] Patent Number: 4,666,432
[45] Date of Patent: May 19, 1987

[54] CATHETER RETAINING MEANS AND METHOD

[76] Inventors: Kenneth McNeish; Marilyn McNeish, both of 3893 E. River Rd., Newtown Falls, Ohio 44444

[21] Appl. No.: 775,576

[22] Filed: Sep. 13, 1985

[51] Int. Cl.[4] .............................................. A61M 25/02
[52] U.S. Cl. .................................. 604/174; 604/179; 604/345; 128/DIG. 26; 128/513
[58] Field of Search .......... 128/132 R, 133, DIG. 26, 128/513; 604/174, 179, 180, 337, 345

[56] References Cited

U.S. PATENT DOCUMENTS

| | | | |
|---|---|---|---|
| 2,476,513 | 7/1949 | Scott | 604/345 |
| 2,612,895 | 10/1952 | Magee | 604/327 |
| 2,624,881 | 1/1953 | Lee | 128/513 |
| 3,078,852 | 2/1963 | Stapleton | 128/513 |
| 4,087,864 | 5/1978 | LaBove et al. | 604/174 X |
| 4,397,641 | 8/1983 | Jacobs | 604/180 |
| 4,419,094 | 12/1983 | Patel | 604/174 |
| 4,578,062 | 3/1986 | Schneider | 604/174 |
| 4,582,508 | 4/1986 | Pavelka | 604/179 |
| 4,596,560 | 6/1986 | Simpson | 604/174 |

OTHER PUBLICATIONS

Raaf—Surgery, Gyne & Obstetrics, Jan. 1985, vol. 158, No. 1, pp. 173–176.

Primary Examiner—Dalton L. Truluck
Attorney, Agent, or Firm—Jacob Trachtman

[57] ABSTRACT

A catheter retaining means and method for a surgically implanted catheter having an internal tubing portion received within the body and an external tubing portion with a free end extending from an exit site on the body. The retaining means comprises a band of flexible material for being received about the body and over the exit site of the implanted catheter for protecting the site of the body and securely retaining in position proximate to the body the external tubing portion as it extends from the exit site. The band has an opening and a pocket overlying the opening for receiving into the pocket through the opening at least a part of the external tubing portion and its free end for storage therein, the pocket allowing the removal therefrom of the free end and part of the external tubing portion of the catheter for placing it in use.

10 Claims, 6 Drawing Figures

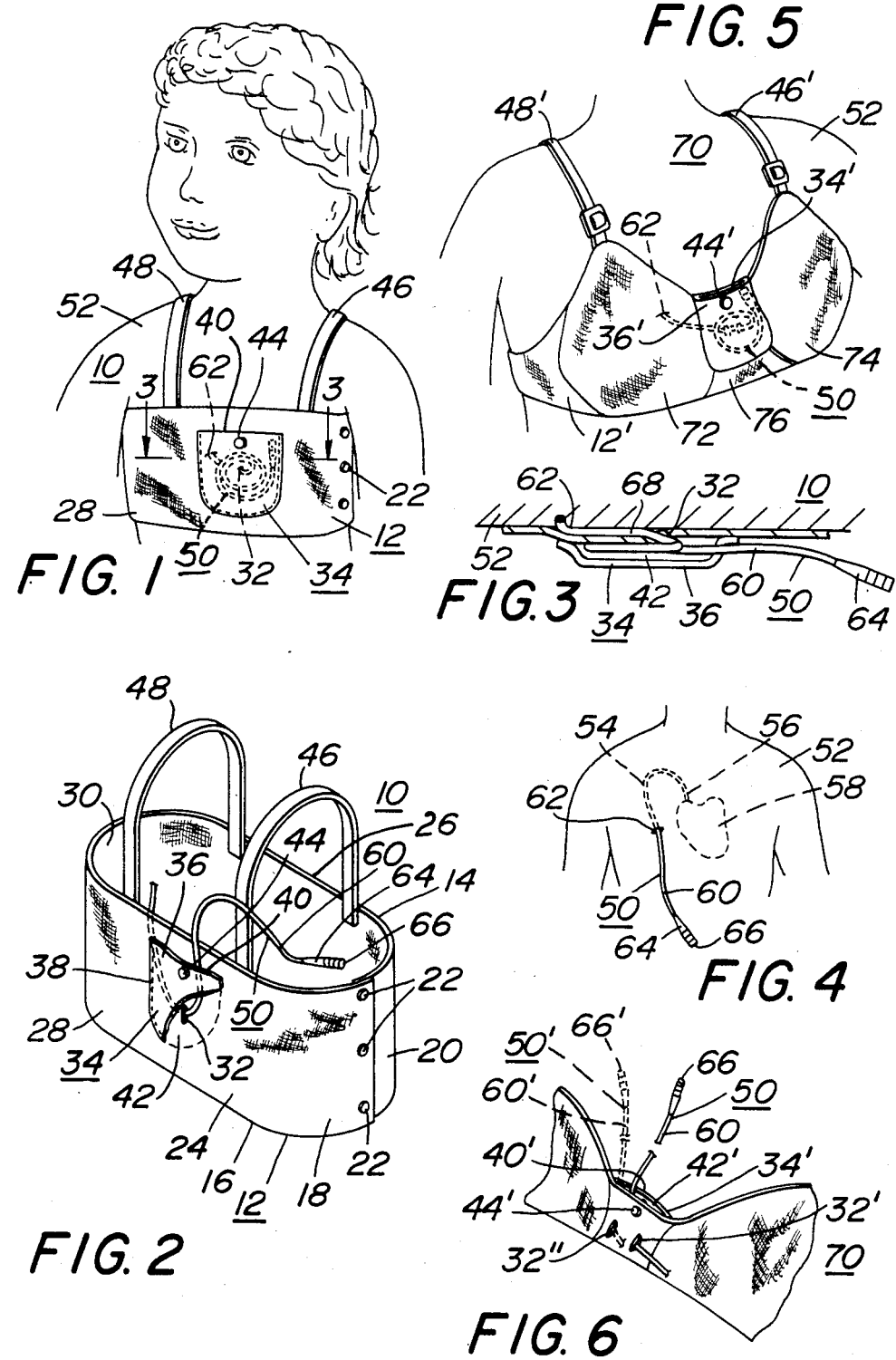

CATHETER RETAINING MEANS AND METHOD

The invention relates to a catheter retaining means and method for retaining an implanted catheter and protecting the exit site of the catheter, and more particularly to a catheter retaining means and method in which the retaining means is received about the body and over the exit site of a surgically implanted catheter for protecting the exit site of the body and retaining in position the external tubing portion of the catheter while allowing the storing and removal for use of the free end and part of the external tubing portion.

BACKGROUND OF THE INVENTION

Surgically implanted catheters such as the Hickman Broviac catheter are used for prolonged treatment of blood disorders by providing a permanent internal tubing portion received into the blood distribution system and particularly proximate to the heart of a subject for the administering of medication and other substances as well as for periodic blood testing. The implantation and use of such catheters are described in detail in the article entitled "Two Broviac Catheters for Intensive Long Term Support of Patients with Cancer" by John H. Raff published in Surgery Gynecology & Obstetrics, January 1984, Volume 158, Number 1, pages 173 to 176. Heretofore, the externally extending catheter tubing portion of the implanted catheter and its free end which extended from an exit site of the body, was taped to the body to prevent displacement and dislodgment of the catheter and to allow maintenance therein of the proper blood level. To use the capped free end of the catheter, it was first necessary to remove the tape securing it to the body. Such removal of tape and retaping to the body each time the catheter was to be used and at least daily to allow the line to be flushed to prevent clogging resulted in sores and irritation of the body. The present means for securing the external portion and end of the catheter is unsuitable because in addition to the sores and irritation which results, the taping does not afford the desired freedom of movement for the patient without fear of dislodging the catheter, and provides an unsightly and disturbing appearance which can produce mental distress in sensitive patients and children rather than the aesthetic appearance which is desirable.

The prior art means, thus, is not suitable for protecting the catheter exit site of the body and for preventing dislodgment and accidental removal of the catheter. This is especially true for patients who are young or who cannot control their movements or who may purposefully move the body about in an excessive manner. Such movements disturb the exit site, cause dislodgment, irritation and displacement of the internally implanted tubing portion of the catheter, and aggravate and cause inflammation of the exit site. The presently utilized retention means is also unsuitable, since it does not allow the use of the end of the external portion of the catheter without the removal of the tape retention means and then reapplication of same to the body after each use of the catheter. This situation is particularly serious where multiple Broviac catheters are utilized as described in the aforereferenced article resulting in increased difficulty and increased pain to the patient as well as greater mental distress.

Since the patient provided with an internally implanted catheter need not be subject to intervention over extended periods of time, it is important that the external portion and its end be stored out of sight and securely retained for permitting the desired freedom of the patient, while still making its use readily available should the need arise. Since at least daily attention must be given to the catheter to keep the line open, such ready accessibility is most important and should be self administrable by the patient should this be necessary.

The catheter retention means may also take the form of an ordinary article of clothing such as a brassiere allowing the subject to wear customary external clothing thereover and making its application unobvious, while still making the external portion of the catheter readily available for use as may be required. The invention also provides a method of applying the catheter retaining means which may easily be accomplished by the user or someone assisting the subject. The catheter retaining means is readily removable for laundering and reapplication with a minimum of effort and without subjecting the patient to pain and irritation prevalent with the utilization of the prior art means and method for retaining the external portion and end of a Broviac type catheter.

SUMMARY OF THE INVENTION

It is therefore a primary object of the invention to provide a new and improved catheter retaining means for firmly retaining a surgically implanted catheter against dislodgment and accidental removal, and protecting its exit site on the body and a method of readily applying the catheter about the body and positioning it over the catheter exit site.

Another object of the invention is to provide a new and improved catheter retaining means and method of applying same to a body which provides protection for the exit site of a surgically implanted catheter, and minimizes movement and dislodgment of the catheter, and does not interfere with the utilization of the catheter or the flow of fluids being infused or drained therethrough.

Another object of the invention is to provide a new and improved catheter retaining means and method of applying same to the body which may be quickly and efficiently applied and minimizes the risk of dislodgment of the catheter or infection and irritation of the exit site.

Another object of the invention is to provide a new and improved catheter retaining means and method of applying same which avoids irritation and pain to the subject in the application and removal of same from the body and readily allows the utilization and storage of the external portion and end of the catheter.

Another object of the invention is to provide a new and improved catheter retaining means and method of application which is readily applied about the torso of the body for retaining in position and protecting the exit site of a Hickman Broviac catheter.

Another object of the invention is to provide a new and improved catheter retaining means and method of applying same which simulates an article of clothing and is comfortable to the user for readily allowing the use and storage of the end and external portion of an implanted catheter.

Another object of the invention is to provide a new and improved catheter retaining means which is garment-like and more visually acceptable to patients by avoiding the appearance of tubing emanating directly from the patients' body.

Another object of the invention is to provide a new and improved catheter retaining means and method of applying same which does not require the use of adhesive materials applied to the body and permits movement of the patient without fear of dislodgment or displacement of the catheter while its external portion is stored or in use.

Another object of the invention is to provide a new and improved catheter retaining means which is especially acceptable to pediatric patients who are frequently frightened by tubing and tape and which allows a patient to view the retaining means as a more normal accessory for his or her person.

Another object of the invention is to provide a new and improved catheter retaining means which provides the desired security to permit the wearer to more normally move the body and engage in activities without fear of displacement or dislodgment of same and the resulting requirement for reinsertion or reimplantation thereof.

Another object of the invention is to provide a new and improved catheter retaining means and method which stabilizes the exit site and removes the fear of interfering with the catheter and its operativeness.

Another object of the invention is to provide a new and improved catheter retaining means and method of applying same which is adaptable for treatment such as chemotherapy by allowing the patient to travel while being assured of the security provided by the catheter retaining means.

Another object of the invention is to provide a new and improved catheter retaining means and method of applying same which is simple in construction, low in cost and which may readily be applied and used by inexperienced persons.

The above objects as well as many other advantages and objects of the invention are achieved by providing a catheter retaining means for application to the exit site of a surgically implanted catheter having an internal tubing portion received within the body and an external tubing portion with a free end extending from an exit site on the body. The catheter retaining means comprises a band of flexible material for being received about the body and over the exit site of the implanted catheter for protecting the site of the body and retaining in position proximate to the body, the external tubing portion as it extends from the exit site. The band has an opening therethrough and a pocket overlying the opening for receiving into the pocket through the opening at least a part of the external tubing portion and its free end for storage therein. The pocket allows the removal therefrom of the free end and part of the external tubing portion of the catheter for placing same in use, and replacement of same into the pocket for storage when not in use. The pocket may also be provided with closure means for its opening for retaining and securing within the pocket the free end and external tubing of the catheter when not in use.

The pocket of the band may be provided by a layer of flexible material secured with the band overlying the opening of the band and leaving a portion unsecured therewith for providing the opening of the pocket, while the securing means may be a snap fastener or other such means for enclosing the opening. The band and pocket of the catheter securing means where desired may be made of an elastic and moisture-absorbent material. The catheter retaining means may also be formed to provide the appearance and usefulness of an article of clothing such as in the form of a brassiere for young girls and women.

In a particular form, the band of the catheter retaining means is provided in a substantially elongated configuration for being received about the torso and has first and second ends with attachment means for detachably securing the ends. This allows the band to be readily applied and removed from the body as well as maintained in position over the exit site of the catheter with the external tubing portion of the catheter extending from the exit site and through the opening communicating with the pocket into which the external end of the catheter is received. In the form of the catheter retaining means for young girls and women, the band may be formed to provide first and second breast supporting portions and an intermediate portion joining the first and second portion. The opening through the band is in its intermediate portion and the pocket overlies the opening in the intermediate portion. The provision of elastic material for at least portions of the band allows the catheter retaining means to be applied to the body by being stretched for applying compressive force over the exit site and to the part of the external portion of the catheter extending between it and the body for firmly retaining and preventing dislodgment and movement of the catheter which is undesirable. In this form, the catheter retaining means also provides the utility of a brassiere and also avoids the unsightly and uncomfortable requirement of using tape for securing the catheter tubing directly with the body. The use of elastic and moisture-absorbent material also provides additional comfort allowing the catheter retaining means to be worn over an extended period of time without requiring removal and replacement.

The method of the invention for retaining a surgically implanted catheter having an internal tubing portion received in the body and an external tubing portion with a free end extending from an exit site of the body comprises the steps of feeding the free end and a part of the external portion of the catheter into a pocket provided by a flexible band by passing the end of the external tubing through an opening in the band communicating with the pocket, and securing the band firmly about the body and over the exit site of the body for protecting the exit site and over the external tubing portion of the catheter which extends from the exit site to the opening in the band for preventing movement and dislodgment of the catheter. The method also includes the steps of removing from the pocket through an opening of the pocket, the end and part of the external portion of the catheter when it is to be used, and the placing the end and part of the extending portion of the catheter into the pocket for storage when not being used. The method further includes the utilization of a substantially elongated band for being received about the body having first and second ends with detachable securing means and securing same in position around the body over the exit site and over the external portion of the catheter extending from the exit site to the opening of the band and firmly retaining the band thereabout by securing together the first and second ends of the band by engaging the detachable securing means. When the band is of an elastic material which is stretchable the method contemplates applying the band over the exit site of the body and after being stretched securing same in position for applying compressive force to the body and the external tubing portion in position between it and the body for firmly retaining the external tubing portion and minimizing disturbance of the exit site and dislodgment of the catheter.

BRIEF DESCRIPTION OF THE DRAWING

The foregoing and other objects of the invention will become more apparent as the following detailed description is read in conjunction with the drawing, in which:

FIG. 1 is a perspective view of a catheter retaining means embodying the invention applied to a child, FIG. 2 is an enlarged perspective view of the catheter retaining means of FIG. 1 illustrating the manner in which the end and external portion of an implanted catheter is fed through the catheter retaining means, FIG. 3 is an enlarged sectional view of a portion of the catheter retaining means taken substantially along line 3—3 of FIG. 1 illustrating the manner in which the band overlies the exit site of the body and retains part of the external portion of the catheter in position against the body and provides access and storage for the end and external portion of the implanted catheter, FIG. 4 illustrates a catheter implanted in a body showing an internal portion received into the body and an external portion and end extending from an exit site of the body prior to application to the body of the catheter retaining means of the invention, FIG. 5 is a perspective view illustrating the invention in the form of a brassiere applied to a subject, and FIG. 6 is an enlarged perspective view of a portion of the catheter retaining means of FIG. 5 showing the inner surface of the device which contacts the body of the patient.

Like reference numerals designate like parts throughout the several views.

DETAILED DESCRIPTION

The FIGS. 1 to 3 illustrate a catheter retaining means 10 embodying the invention. The retaining means 10 comprises a band 12 of flexible material, preferably a woven fiber material, in the form of an elongated substantially rectangular sheet. The band 12 has upper and lower edges 14 and 16 and end portions 18 and 20 provided with fastening means 22. When the ends 18 and 20 are secured together by the fastening means such as snap fasteners 22, micro-hook or other securing means, the band 12 provides an enclosed continuous form providing a front panel 24 and a rear panel 26. The band 22 in its closed configuration shown in FIG. 2 provides an outer surface 28 and an inner surface 30.

The front panel 24 has an opening 32 in the form of a slit therein extending between its inner surface 30 and outer surface 28. A pocket 34 is provided by a sheet of flexible material 36 overlying the opening 32 and secured as by stitches 38 with the front panel 24 of the band 12 over its outer surface 28. The sheet 36 is stitched along its side and bottom edges to form a pocket enclosed on all sides except the top edge 40 which provides an opening of the pocket 34. The space between the sheet 36 and the outer surface 28 of the band 12 forms a cavity 42 or inside retaining space of the pocket 34. The top edge 40 of the pocket 34 may be provided with a snap fastener 44, micro-hook or other securing means for enclosing the pocket 34. If desired the band 12 may also be provided with a pair of shoulder straps 46, 48, each having ends secured with the inner surface 30 between the front and back panels 28 and 30 of the band 12.

In operation, the catheter retaining means 10 is used for retaining the external tubing portion of a surgically implanted catheter which extends from an exit site on the body. Catheters of this type used for the administration of chemotherapy intravenously in the treatment of patients with cancer, such as the Hickman Broviac catheters, are described in the article entitled "Two Broviac Catheters for Intensive Long Term Support of Patients with Cancer" by John R. Raaf referred to above. Such catheters allow the delivery of drugs and other materials directly into the vascular system of a patient by placing the implanted end of the catheter into the superior vena cava with the tip of the catheter positioned to lie in the right atrium or lower superior vena cava. In cases where there are sufficient future access requirements two Broviac catheters are implanted simultaneously for insuring access in the event that a catheter becomes "positional" so that blood samples cannot be drawn. Such dual simultaneous Broviac catheter placement has been provided to adult patients who require prolonged intravenous support while receiving chemotherapy or a bone marrow transplant. Patients can be taught to care for the catheters following their discharge from the health treatment facility and the majority of catheters can be used for outpatient treatment.

FIG. 4 illustrates the implantation of a catheter 50 in the body 52 of a patient. The catheter 50 has an internal tubing portion 54 received into the body with its tip 56 position in the right atrium of the heart 58 while the external tubing portion 60 of the catheter 50 extends from an exit site 62 in the chest of the body 52 of the patient which is displaced to the right of center on the body. The opening 62 in the body may be sutured to assist in retaining the catheter 50 in position within the body and also to minimize seepage of body fluids therethrough. The externally extending tubing 60 has a free end 64 which is enlarged and provided with a removable closure cap 66. When the catheter 50 is to be used for infusing or withdrawing fluids from the body, the cap 66 is removed for this purpose and then replaced. Such use may take place at various times, and when the catheter is used only infrequently steps must be taken to maintain the lines free by administering heparin solution through the free end 64 of the catheter 50.

Subjecting the external tubing portion 60 of the catheter 50 to various forces and movements which are unavoidable, either when the catheter is in use or when it is not in use, results in inflammation of the exit site 62 and may cause dislodgment of the catheter and its implanted tip 56 from its desired position. Such a dislodgment, often also results in blocking the tip 56. This causes the catheter to become "positional" preventing the drawing of blood and rendering the catheter non-operational for this purpose. In order to minimize the exertion of force, and the movement and dislodgment of the catheter, the external portion 60 of the catheter has in prior practice been taped directly to the skin of the body with the capped end 64 positioned upwardly. This requires the removal of the tape at least for the daily flushing of the tubing of the catheter or for the other required purposes, and the replacement after each such use of the tape for retaining and securing the catheter tubing to the body. This prior practice has resulted in sores and irritation as well as pain to the patient with each such removal and reapplication.

The catheter retaining means 10 of the invention removes the requirement for the extensive taping of the external tubing of the catheter to the body for stabilizing its position, and allows the use of a small dressing provided by a 2-inch square of sterile pad held in place by 2 thin strips of tape ½ inch wide over the exit site 62 to absorb body fluids emanating therefrom and to prevent foreign matter from contaminating the exit site 62. The catheter retaining means 10 when applied to the body of the patient retains the external tubing portion 60 of the catheter 50 against movement and minimizes irritation to the body at the exit site or dislodgment of the catheter and the position of its tip 56 within the body. FIG. 1 illustrates the application of the catheter retaining means 10 to the body which can be readily achieved by attaching the fasteners 22 at the ends 18 and 20 of the band 12 to secure it in place about the body 52 of the patient. The front panel is positioned over the chest to cover the exit site 62 of the body with the pocket centrally positioned on the chest. Prior to fastening the ends 18 and 20 of the band 12, the end 64 of the external tubing portion 60 of the catheter 50 is fed through the opening 32 of the band 12 into the cavity 42 of the pocket 34 with the free end 64 extending out through the opening provided at the top edge 40 of the pocket 34. The end 64 is drawn through the pocket 32 so that any excess of the tubing portion 60 is pulled through the slit 32 until the portion 68 of the tubing which remains lies flat against the surface of the body 52 and the inner surface 30 of the band 12 as shown in FIG. 3. The fasteners 22 are then engaged so that the inner surface 30 of the band 12 firmly contacts and engages the body and compresses between it and the body 52 the portion 68 of the external tubing 60 for firmly retaining it and minimizing movement and dislodgment thereof. The catheter 50 may be utilized by removing the cap 66 at the end 64 when the external portion of the catheter 50 is removed from the pocket 34 as illustrated in FIG. 2. When the catheter 50 is not in use, the cap 66 is replaced and with the snap 44 open, the part of the tubing of the catheter 50 which extends out of the pocket 34 is formed into a coil and placed within the pocket 34 as shown in FIG. 1, and the snap secured for retaining same for storage therewithin. When the catheter is not in use, the catheter retaining means 10 conceals the catheter while making same readily available for use when required, and provides the appearance of a garment which may have the straps 46 and 48 for assisting in retaining it in position about the chest.

When the catheter retaining means 50 requires removal or replacement, this is easily achieved by detaching the snap fasteners 22 and 44, uncoiling the tubing portion of the catheter 50 stored within the pocket 34 and extending it linearly, after which it may easily be withdrawn from the pocket through the opening 32 in the band 12. The band 12 of retaining means 10 may then be easily removed from the body without any discomfort to the patient and avoiding the sores and irritations which would otherwise result from the use of tape applied directly to the patient's skin. The removed retaining means 10 may be laundered and reused as would be done with any other washable article of clothing. The catheter retaining means 10 may be provided in various sizes and arrangements required or desirable for the particular utilization. The band 12 also may be provided with a series of closure means permitting adjustment of size as required, while the use of micro-hooks on the end portions 18 and 20 would allow the band 12 to be wrapped around the chest and the ends secured to accommodate the various sizes or girths of the body and to apply the desired compressive force for retaining the catheter in the desired position while minimizing the dislodgment of same.

The band 12 of the retaining means 10 may also be made of an elastic material so that it can be stretched for engaging the fasteners 22. This results in the exertion of a compressive force on the body serving to firmly retain the catheter in position as it extends from the exit site 62 of the body 52 between the body and the inner surface 30 of the band 12 for minimizing movement and dislodgment of the catheter 50. For this purpose the sheet material 36 of the pocket 34 may also be made of a stretchable material. In addition, where desired, the band 12 may be made of a smooth and absorbent material for increasing the comfort of the wearer.

The FIGS. 5 and 6 illustrate a catheter retaining means 70 embodying the invention which is a modified form of the retaining means 10. The retaining means 70 is in the form of a brassiere suitable for use by young girls or women comprising a band 12' for extending about the body over the exit site 62 and having adjustable supporting straps 46' and 48' and first and second breast supporting portions 72 and 74 joined by an intermediate portion 76. The intermediate portion 76 of the band 12' is provided with an opening 32' in the form of a slit and the sheet of material 36' over the central portion 76 overlies the slit 32' and forms a cavity 42' for receiving and storing the external tubing portion 60 of the catheter 50 when not in use. The pocket 34' is also provided with an open top edge 40' which is secured by a snap fastener 44' or other suitable closure means. The central portion 76 may also be provided with a second opening 32" in the form of a slit for receiving therethrough, as does the first slit 32', the external portion 60' of a second catheter 50,' in the case where two catheters are simultaneously implanted in the patient. In this case, the pocket 34' is provided with sufficient capacity to receive and retain therein the external portions 60 and 60' of catheters 50 and 50' in their coiled configurations as shown in FIG. 5. In use, the snap fastener 44' may be released for removing either one or both of the ends 66, 66' of the catheters 50 and 50' when they are to be used, and thereafter replaced in the cavity 42' of the pocket 34' for storage. The catheter retaining means 70, thus, serves a dual purpose of providing a useful article of apparel as well as a catheter retaining means and is applied to the body by threading one or more catheters 50, 50' through the openings 32', 32" into the cavity 42' of the pocket 34' as described in connection with the catheter retaining means 10. The band 12' in the catheter retaining means 70 may also be made of a flexible stretchable material having a smooth surface and being absorbent for providing the advantages noted above in connection with the retaining device 10.

The catheter retaining means 10 and 70, thus, provide the advantages and achieve the objects of the invention noted above and may be modified for meeting the particular requirements of the application. It will, thus, of course be understood that the description and drawings herein contained are illustrative merely, and that various modifications and changes may be made in the structures and methods disclosed without departing from the spirit of the invention.

What is claimed is:

1. A catheter retaining means for a surgically implanted catheter having an internal tubing portion received within the body and an external tubing portion with a free end extending from an exit site on the body comprising a band of flexible material having an outer surface and an inner surface for being received and secured about the body and covering the exit site of an implanted catheter for protecting the site of the body, the inner surface of the band overlying and retaining in a position proximate to and along the surface of the body the external tubing portion of the catheter as it extends from the exit site, the band having an opening extending between its outer and inner surfaces sized to snugly receive therethrough the external portion of the catheter and a pocket overlying the outer surface and the opening for receiving into the pocket through the opening at least a part of the external tubing portion and its free end for storage therein, the pocket covering and concealing the opening of the band while allowing the removal therefrom of the free end and part of the external tubing portion of the catheter for placing it in use while the retaining means remains about the body and over the exit site, the pocket having an opening displaced from and unaligned with the opening of the band for allowing the removal from the pocket of the free end and part of the external tubing portion of the catheter for placing it in use and for replacing same into the pocket for storage when not in use, and the band having a substantially elongated configuration with first and second ends and attachment means for detachably securing together its ends for maintaining the band in position about the body and over the exit site of the body and external tubing portion of the catheter as it extends from the exit site.

2. The catheter retaining means of claim 1 in which the band is of elastic material.

3. The catheter retaining means of claim 1 in which the pocket includes closure means for its opening for retaining therein the free end and external tubing.

4. The catheter retaining means of claim 4 in which the pocket comprises a layer of flexible material secured with the band overlying and concealing from view the opening of the band and leaving a portion unsecured therewith for providing the opening of the pocket which is displaced from and unaligned with the opening of the band.

5. The catheter retaining means of claim 4 in which the pocket includes closure means for its opening for retaining therein the free end and external tubing.

6. The catheter means of claim 4 in which the band and pocket are of an elastic and moisture absorbent material.

7. The catheter retaining means of claim 1 in which the band has first and second breast supporting portions and an intermediate portion joining the first and second portions, the intermediate portion having the opening of the band and the pocket overlying the opening.

8. The catheter retaining means of claim 7 in which the pocket comprises a layer of flexible material secured with the band overlying and concealing from view the opening of the band and leaving a portion unsecured therewith for providing the opening of the pocket which is displaced from and unaligned with the opening of the band.

9. The catheter retaining means of claim 8 in which the pocket includes closure means for its opening for retaining therein the free end and external tubing.

10. The catheter retaining means of claim 9 in which the band and pocket are of an elastic and moisture absorbent material.

* * * * *